(12) United States Patent
Lee et al.

(10) Patent No.: US 11,376,157 B2
(45) Date of Patent: Jul. 5, 2022

(54) VITRECTOMY SURGICAL APPARATUS WITH CUT TIMING BASED ON PRESSURES ENCOUNTERED

(71) Applicant: Johnson & Johnson Surgical Vision, Inc., Irvine, CA (US)

(72) Inventors: Fred C. Lee, Irvine, CA (US); James B. Gerg, Lake Forest, CA (US); Kyle E. Lynn, Tustin, CA (US); Zheng Zhang, Laguna Beach, CA (US); Lauren M. Hickey, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 416 days.

(21) Appl. No.: 16/425,851

(22) Filed: May 29, 2019

(65) Prior Publication Data
US 2019/0274880 A1    Sep. 12, 2019

Related U.S. Application Data

(60) Continuation of application No. 15/354,204, filed on Nov. 17, 2016, now Pat. No. 10,307,291, which is a
(Continued)

(51) Int. Cl.
*A61F 9/007* (2006.01)
*A61B 17/3205* (2006.01)
*A61B 17/00* (2006.01)

(52) U.S. Cl.
CPC ...... *A61F 9/00763* (2013.01); *A61B 17/3205* (2013.01); *A61F 9/00736* (2013.01);
(Continued)

(58) Field of Classification Search
CPC .............. A61F 9/00736; A61F 9/00763; A61F 9/00709; A61F 9/00745; A61B 17/3205; A61B 2017/00544
See application file for complete search history.

(56) References Cited

U.S. PATENT DOCUMENTS 3,559,970 A    2/1971 Ichizo et al.
3,882,872 A    5/1975 Douvas et al.
(Continued)

FOREIGN PATENT DOCUMENTS

WO    2008079526 A2    7/2008
WO    2011149621 A1    12/2011
(Continued)

OTHER PUBLICATIONS

International Search Report and Written Opinion for Application No. PCT/US2013/075771, dated Apr. 2, 2014, 13 pages.
(Continued)

*Primary Examiner* — Thomas McEvoy
(74) *Attorney, Agent, or Firm* — Johnson & Johnson Surgical Vision, Inc.

(57) ABSTRACT

A vitrectomy apparatus is provided, including a pressure source, a cut valve connected to the pressure source, the cut valve configured to be turned on and off to provide pressure to selectively extend and retract a vitrectomy cutting device, a sensor configured to sense pressure provided from the cut valve, and a controller configured to control operation of the cut valve based on pressure sensed by the sensor. The controller is configured to monitor pressures encountered and alter cut valve timing based on pressure conditions previously encountered.

8 Claims, 9 Drawing Sheets

Related U.S. Application Data division of application No. 13/717,021, filed on Dec. 17, 2012, now Pat. No. 9,498,376.

(52) U.S. Cl.
CPC .............. *A61B 2017/00017* (2013.01); *A61B 2017/00022* (2013.01); *A61B 2017/00544* (2013.01)

(56) References Cited

U.S. PATENT DOCUMENTS

| | | |
|---|---|---|
| 4,314,560 A | 2/1982 | Helfgott et al. |
| 4,768,506 A | 9/1988 | Parker et al. |
| 5,279,547 A | 1/1994 | Costin |
| 5,403,276 A | 4/1995 | Schechter et al. |
| 5,417,246 A | 5/1995 | Perkins et al. |
| 5,549,139 A | 8/1996 | Perkins et al. |
| 5,788,667 A | 8/1998 | Stoller |
| 5,857,485 A | 1/1999 | Perkins et al. |
| 5,979,494 A | 11/1999 | Perkins et al. |
| 6,010,496 A | 1/2000 | Appelbaum et al. |
| 6,258,111 B1 | 7/2001 | Ross et al. |
| 6,290,690 B1 | 9/2001 | Huculak |
| 6,506,176 B1 | 1/2003 | Mittelstein et al. |
| 6,575,990 B1 | 6/2003 | Wang et al. |
| 6,599,271 B1 | 7/2003 | Easley |
| 6,599,277 B2 | 7/2003 | Neubert |
| 6,689,089 B1 | 2/2004 | Tiedtke et al. |
| 7,335,217 B2 | 2/2008 | Wang et al. |
| 8,460,324 B2 | 6/2013 | Gerg et al. |
| 8,818,564 B2 | 8/2014 | Zhou et al. |
| 8,986,332 B2 | 3/2015 | Gerg et al. |
| 10,758,411 B2 | 9/2020 | Dean et al. |
| 2001/0029335 A1 | 10/2001 | Juan et al. |
| 2002/0173814 A1 | 11/2002 | Jung et al. |
| 2003/0195538 A1 | 10/2003 | Wang et al. |
| 2005/0096682 A1 | 5/2005 | Daffer |
| 2005/0113715 A1 | 5/2005 | Schwindt et al. |
| 2007/0078506 A1 | 4/2007 | McCormick et al. |
| 2007/0088376 A1 | 4/2007 | Zacharias |
| 2008/0114372 A1 | 5/2008 | Edwards et al. |
| 2008/0146988 A1 | 6/2008 | Olivera et al. |
| 2008/0154292 A1 | 6/2008 | Huculak et al. |
| 2008/0208207 A1 | 8/2008 | Huculak et al. |
| 2008/0208233 A1 | 8/2008 | Barnes et al. |
| 2009/0143734 A1 | 6/2009 | Humayun et al. |
| 2009/0259242 A1 | 10/2009 | Gerg et al. |
| 2010/0156646 A1 | 6/2010 | Cull et al. |
| 2011/0054508 A1 | 3/2011 | Zhou et al. |
| 2011/0077626 A1 | 3/2011 | Baerveldt et al. |
| 2011/0144675 A1 | 6/2011 | Gao et al. |
| 2011/0295293 A1 | 12/2011 | Agahi |
| 2011/0295296 A1 | 12/2011 | Charles |
| 2012/0053486 A1 | 3/2012 | Huculak |
| 2012/0157879 A1 | 6/2012 | Mark et al. |
| 2012/0157906 A1 | 6/2012 | Underwood et al. |
| 2012/0158029 A1 | 6/2012 | Underwood et al. |
| 2012/0158030 A1 | 6/2012 | Underwood et al. |
| 2012/0165724 A1 | 6/2012 | Auld et al. |
| 2012/0310146 A1 | 12/2012 | Easley |
| 2013/0060210 A1 | 3/2013 | Ross et al. |
| 2013/0144317 A1 | 6/2013 | Valencia |
| 2013/0158578 A1 | 6/2013 | Ghodke et al. |
| 2014/0114336 A1 | 4/2014 | Schmitz et al. |
| 2014/0171991 A1 | 6/2014 | Lee et al. |
| 2014/0171993 A1 | 6/2014 | Lynn et al. |
| 2015/0148836 A1 | 5/2015 | Heeren |

FOREIGN PATENT DOCUMENTS

| | | |
|---|---|---|
| WO | 2014099982 A1 | 6/2014 |
| WO | 2014099993 A1 | 6/2014 |
| WO | 2014105531 A1 | 7/2014 |

OTHER PUBLICATIONS

International Search Report and Written Opinion for Application No. PCT/US2013/075788, dated Apr. 3, 2014, 13 pages.

International Search Report and Written Opinion for Application No. PCT/US2013/075815, dated Apr. 24, 2014, 14 pages.

International Search Report for Application No. PCT/US2015/027012, dated Jun. 25, 2015, 5 pages.

Written Opinion for Application No. PCT/US2015/027012, dated Jun. 25, 2015, 8 pages.

VITRECTOMY SURGICAL APPARATUS WITH CUT TIMING BASED ON PRESSURES ENCOUNTERED

This application is a continuation of and claims priority to U.S. patent application Ser. No. 15/354,204, filed Nov. 17, 2016, which is a divisional of and claims priority to U.S. patent application Ser. No. 13/717,021, filed Dec. 17, 2012, the entire contents of which are incorporated herein by reference.

U.S. patent application Ser. No. 13/717,021 was filed concurrently with the following applications, both of which are incorporated herein by reference:

"Vitrectomy Surgical Apparatus", inventors Fred Lee, et al., U.S. application Ser. No. 13/717,071, and issued on Nov. 8, 2016 as U.S. Pat. No. 9,486,358; and "Vitrectomy Surgical Apparatus with Regulating of Material Processed", inventors Kyle Lynn, et al., U.S. application Ser. No. 13/717,044, and issued on Mar. 1, 2016 as U.S. Pat. No. 9,271,867.

BACKGROUND

Field

The present invention relates generally to the field of surgical repair of retinal disorders, and more specifically to pneumatic vitrectomy operation during ophthalmic surgical procedures.

Background

The present invention relates generally to the field of surgical repair of retinal disorders, and more specifically to pneumatic vitrectomy operation during ophthalmic surgical procedures.

Background

Vitrectomy surgery has been successfully employed in the treatment of certain ocular problems, such as retinal detachments, resulting from tears or holes in the retina. Vitrectomy surgery typically involves removal of vitreous gel and may utilize three small incisions in the pars plana of the patient's eye. These incisions allow the surgeon to pass three separate instruments into the patient's eye to affect the ocular procedure. The surgical instruments typically include a vitreous cutting device, an illumination source, and an infusion port.

Current vitreous cutting devices may employ a "guillotine" type action wherein a sharp-ended inner rigid cutting tube moves axially inside an outer sheathing tube. When the sharp-ended inner tube moves past the forward edge of a side port opening in the outer sheathing tube, the eye material (e.g. vitreous gel or fibers) is cleaved into sections small enough to be removed through the hollow center of the inner cutting tube. Vitreous cutters are available in either electric or pneumatic form. Today's electric cutters may operate within a range of speeds typically between 750-2500 cuts-per-minute (CPM) where pneumatic cutters may operate over a range of speeds between 100-2500 CPM. The surgeon may make adjustments to control the pneumatic vitrectomy surgical instrument cutting speed, i.e. controlling the cutting device within the handpiece, in order to perform different activities during the corrective procedure. Corrective procedures may include correction of macular degeneration, retinal detachment, macular pucker, and addressing eye injuries.

The cutting device within a pneumatic handpiece requires precise control of applied pressure to overcome the internal spring return mechanism to assure the quality of each cutting stroke. Today's systems typically employ a constant opening signal time to open the valve at low cutting speeds. As the selected cutting speed increases, reducing the amount of time the valve is opened is often necessary to prevent constant over-pressurizing of the handpiece at the forward end of the cutting stroke. The frequency of opening and closing the pneumatic valve, i.e. the time interval between each opening cycle of the valve, is varied to achieve the desired cutting speed.

Although most designs use variable valve opening timing and variable timing between valve openings for pneumatic vitrectomy cutter control, certain advanced designs vary the input pneumatic supply pressure as vitrectomy cutter speed changes. Such operation can enhance the quality and efficiency of material processed by the vitrectomy cutter during each cut cycle. The fundamental limitation of a variable input supply pressure vitrectomy cutter control is the shortest amount of time that the air volume in the cutter body and the associated tube set may be pressurized to reach the minimum peak pressure required to advance the cutter to a cut position and then vent to reach the minimum residual pressure to allow the spring-loaded cutter to return to a retracted position. Again, current pneumatic designs are limited to cutting speeds within a range of approximately 100 to 2500 CPMs.

Further, current vitrectomy systems typically compensate for mechanical delays by providing excess pressure to extend the cutter and/or allocating excess time to retract the cutter. This type of operation is based on historical performance and some conjecture that the present situation is similar to past situations. Such operation and use of power and/or timing buffers are not optimal. Further, a certain amount of material is typically brought into the cutter based on the aspiration rate and the amount of time the cutter is open or closed, which is related to the pressure supplied to the cutter during each cut cycle. Such designs cut based on scheduled timing, resulting in more or less material cut than desired.

Today's vitrectomy surgical systems require a wide range of selectable cutting speeds and highly accurate control of the amount of pressure supplied is desirable to ensure proper instrument handpiece control and safe use in an operating theater. It may be beneficial in certain circumstances to offer the surgeon enhanced accuracy in cutting speeds, cutting efficiency, controllability, and other attributes related to performance of the vitrectomy procedure. Further, in certain circumstances benefits may be obtained by adjusting operation based on conditions encountered rather than establishing and employing operational parameters irrespective of such conditions, including altering operational parameters such as cut rate, amount of material cut, and other critical vitrectomy parameters.

Based on the foregoing, it would be advantageous to provide a system that enables pneumatic cutting functionality at cutting speeds at or higher than those achievable with today's vitrectomy surgical instrument systems. Such a design would benefit from options offered that provide more effective and efficient cutting parameters as compared with prior designs.

SUMMARY

Thus according to one aspect of the present invention, there is provided a vitrectomy apparatus including a pressure source, a cut valve connected to the pressure source, the cut valve configured to be turned on and off to provide pressure to selectively extend and retract a vitrectomy cutting device, a sensor configured to sense pressure provided from the cut valve, and a controller configured to control operation of the cut valve based on pressure sensed by the sensor. The controller is configured to monitor pressures encountered and alter cut valve timing based on pressure conditions previously encountered.

Other features and advantages of the present invention should be apparent from the following description of exemplary embodiments, which illustrate, by way of example, aspects of the invention.

DETAILED DESCRIPTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design provides a system and method for high-speed pneumatic vitrectomy control and operation that employs parameters encountered to more accurately and efficiently cut the vitreous material.

The present design is directed to accurate, reliable, and efficient control of the forward and backward reciprocating motion cutting speed of the blade in a pneumatic vitrectomy handpiece used in a medical instrument system. The present design will be discussed herein with a particular emphasis on a medical or hospital environment, where a surgeon or health care practitioner performs. For example, an embodiment of the present design is a phacoemulsification surgical system that comprises an integrated high-speed control module for the vitrectomy handpiece. The surgeon may adjust or set the cutting speed via a graphical user interface (GUI) module or a foot pedal switch to control the high-speed pneumatic vitrectomy handpiece.

System

Figure 1A:
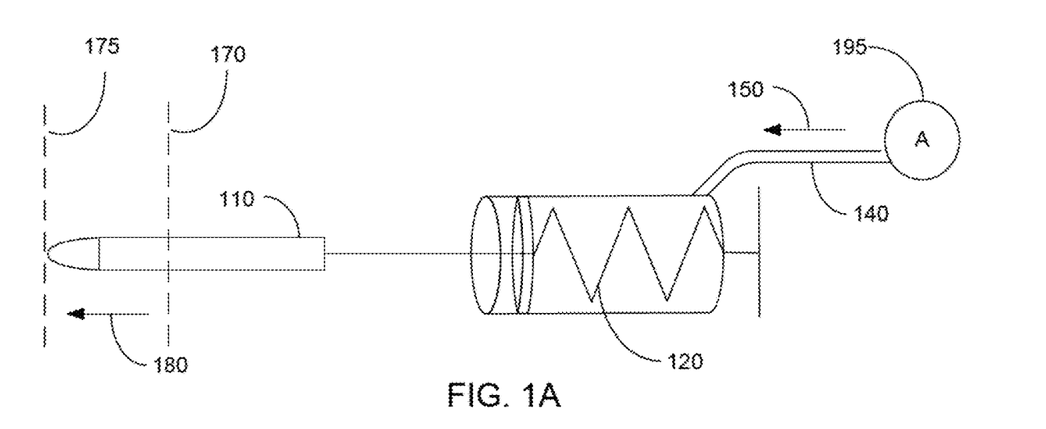
FIG. 1A illustrates a common vitrectomy system's pneumatic cutting mechanism, located within a surgical handpiece, with the pneumatic cutting mechanism extended in a "cut," "closed port," or "forward" position.
Figure 1B:
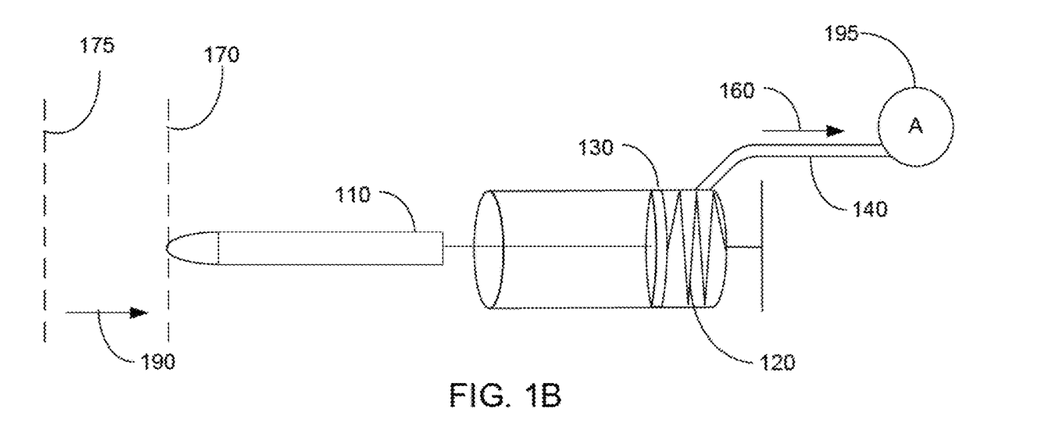
FIG. 1B shows a common vitrectomy system's pneumatic cutting mechanism, located within a surgical handpiece, with the pneumatic cutting mechanism spring retracted in an "initial," "open port," or "backward" position.

FIGS. 1A and 1B are high-level conceptual block diagrams illustrating a common vitrectomy system's pneumatic cutting mechanism located within a surgical handpiece provided for purposes of explaining the present invention. FIG. 1A shows the pneumatic cutting mechanism in the "cut," "closed port," or "forward" position, while FIG. 1B shows the pneumatic cutting mechanism in the "initial," "open port," or "backward" position. Referring to FIG. 1A, construction of pneumatic cutter devices typically involve a blade 110 positioned to work or operate against a spring 120 by inflating and deflating a bladder 130 configured to move blade 110 by 'pushing' blade 110 forward to a forward position 175 when bladder 130 is inflated and 'pulling' blade 110 backward using the energy stored in spring 120 to its resting position or initial position 170 when bladder 130 is deflated. The desired cutting speed may be realized by filling and emptying bladder 130 in a cyclical manner through an air passage 140 arranged for receiving a pressurized airburst in the direction indicated at point 150. The received pressurized air burst is then evacuated or vented in direction 160.

Current designs are generally configured to cyclically inflate and deflate bladder 130 to move blade 110 in a forward direction 180 and backward direction 190, thus producing the desired cutting action. A combination input pressurized air supply and output air venting valve mechanism 195, or valve, is represented in FIGS. 1A and 1B.

In order to control the speed of blade 110, currently available pneumatic designs typically use a control signal to open and close valve 195. Valve 195 may be configured to provide a pressurized airburst when the valve is open, filling bladder 130 and venting the air within bladder 130 when the valve is closed to empty the bladder. Increasing the frequency of the control signal cycling rate, which produces a shorter pressurized air burst time, generally results in an increased cutting speed, or an increased number of cuts-per-minute as observed at the knife. A subsequent decrease in control signal cycling rate generally produces a slower or decreased cutting speed.

Figure 2A:
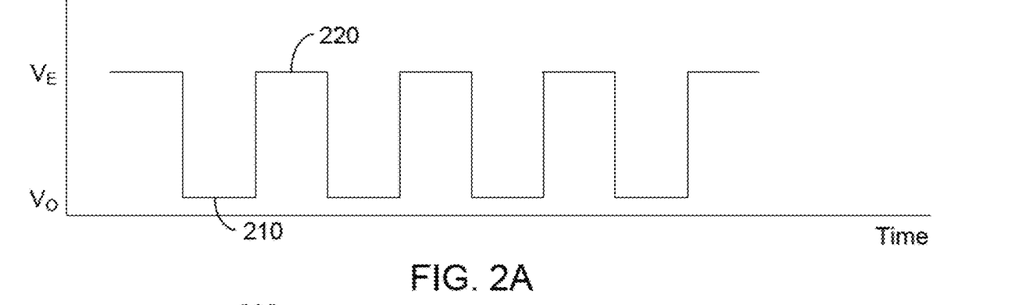
FIG. 2A is a graph illustrating a typical cyclical control signal used for opening and closing a valve by setting the valve to either an energizing or a de-energizing state.
Figure 2B:
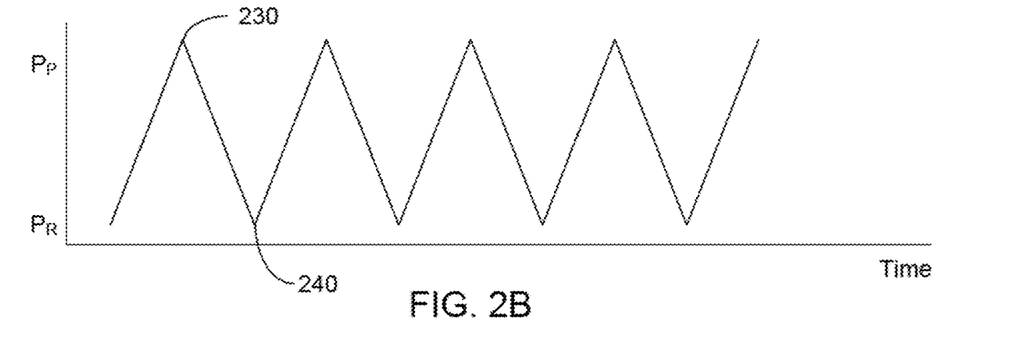
FIG. 2B is a graph illustrating an output pressure waveform resulting from the control signal illustrated in FIG. 2A.

Previous designs have employed control signals to drive the cutter. One example control signal to instruct the opening and closing of valve 195 associated with air passage 140 is shown in FIG. 2A. The control signal illustrated in FIG. 2A may cycle between valve-off ($V_O$) at point 210 and valve-on ($V_E$) at point 220, or provide a valve-energized instruction at a predetermined cycling rate, thereby effectuating the desired cutting speed. FIG. 2B illustrates an example pressure waveform resulting from the application of the control signal shown in FIG. 2A. The waveform is shown to have a constant rise in pressure up to a peak pressure ($P_P$) at 230 when the valve is energized. A subsequent drop in pressure to a residual pressure ($P_R$) at point 240 occurs when the valve is de-energized. The cycling in pressure, for controlling the blade forward and backward reciprocating movements, as illustrated by the waveform shown in FIG. 2B, may produce a specific cutting speed for blade 110 in terms of cuts-per-minute.

Pneumatic cutter designs have been configured with a speed control device to select and vary the rate the blade mechanism moves forward and backward to effectuate cutting. In these designs, changing the speed of the blade may involve varying the time or duration of the control signal provided to the valve. By increasing the open period and closed period of valve 195, the resultant blade speed is reduced. Likewise, decreasing the amount of time valve 195 is open and closed causes the blade speed to increase.

Figure 2C:
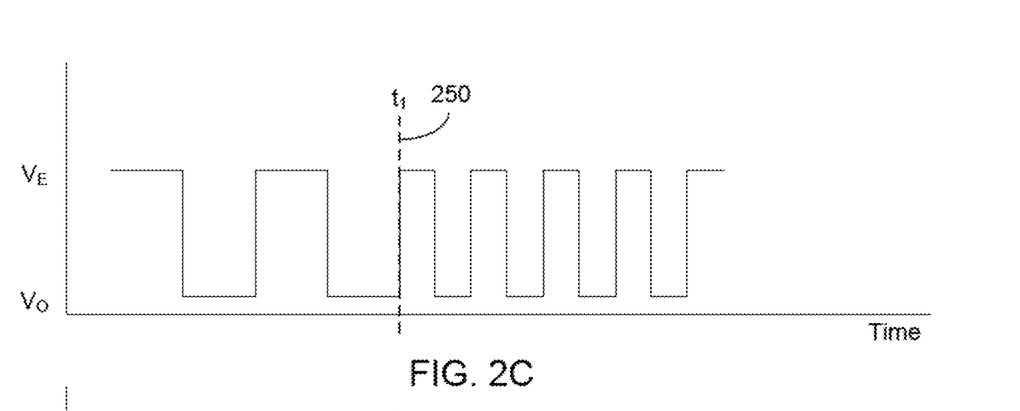
FIG. 2C is a graph illustrating the cyclical control signal applied to a valve where at a specific instance in time the frequency is increased.
Figure 2D:
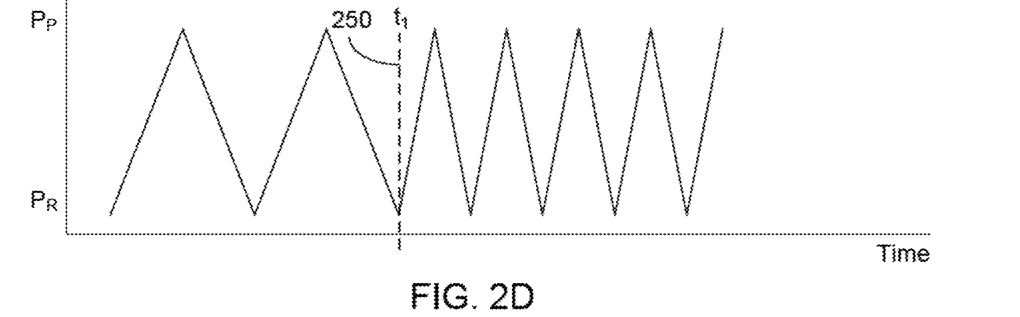
FIG. 2D is a graph illustrating a pressure waveform resulting from the change in the cyclical control signal frequency as illustrated in FIG. 2C.

An example of a control signal for controlling the filling and emptying of air in bladder 130 with an increase in cycle time is illustrated in FIG. 2C. Before time ti at 250, the control signal cyclic frequency is set at a lower rate than after time ti to illustrate the surgeon selecting an increase in cutting speed at time ti during a surgical procedure. FIG. 2D illustrates an example pressure waveform resulting from the application of the control signal shown in FIG. 2C. This pressure waveform reflects the control signal change that occurred at time ti at 250, and may drive blade 110 at a faster rate.

The pneumatic vitrectomy handpiece is used in connection with a phaco-vitrectomy module and may be part of a phacoemulsification machine. Such a handpiece may include a "guillotine" type cutter pneumatically driven to either an open or closed position. Opening and closing occurs via air pressure provided via a flexible line or delivery line between the cutter and a pneumatic driver. The pneumatic driver may include a pressure source, such as a pump, configured to fill a small reservoir with compressed air at its maximum pressure capacity. The output of this reservoir is connected to a pressure regulator that may regulate the air pressure down to the level required by the cutter, as shown by peak $P_P$ and residual $P_R$ pressure in FIG. 2B. A smaller reservoir may be supplied or fed by the regulator output, forming the source for the delivery valve.

The electronic controller may be connected to the delivery valve and may provide instructions to produce a pulse width (in time) of pressurized air when the valve is open. The controller may be arranged to provide fixed pulses of pressurized air within the flexible line in a manner that drives the cutter. The electronic controller may use a fixed pulse timing control signal to instruct the delivery valve to open and close. The fixed timing, or fixed duration, control signal instructs the delivery valve to open and close in a constant cyclical manner. When the flexible line is at zero or near zero pressure, for example refer to residual pressure $P_R$ shown in FIG. 2B, the cutter is biased toward the initial or resting position. The cutter closes when the air pressure in the cutter delivery line exceeds a predetermined value between $P_R$ and $P_P$. When the delivery valve is off, the air in the cutter tubing is exhausted through the valve exhaust port. The cutter then returns to the initial position when the pressure in the delivery line decreases close to atmospheric pressure, i.e. $P_R$.

The foregoing description generally discloses the components and control functionality of prior vitrectomy devices. Such control functionality can be characterized as "open-loop," or without any type of feedback. Cutting speeds, etc. are simply set by a surgeon or user and effectuated, and changes in conditions or parameters in the environment are unaccounted for.

Figure 3A:
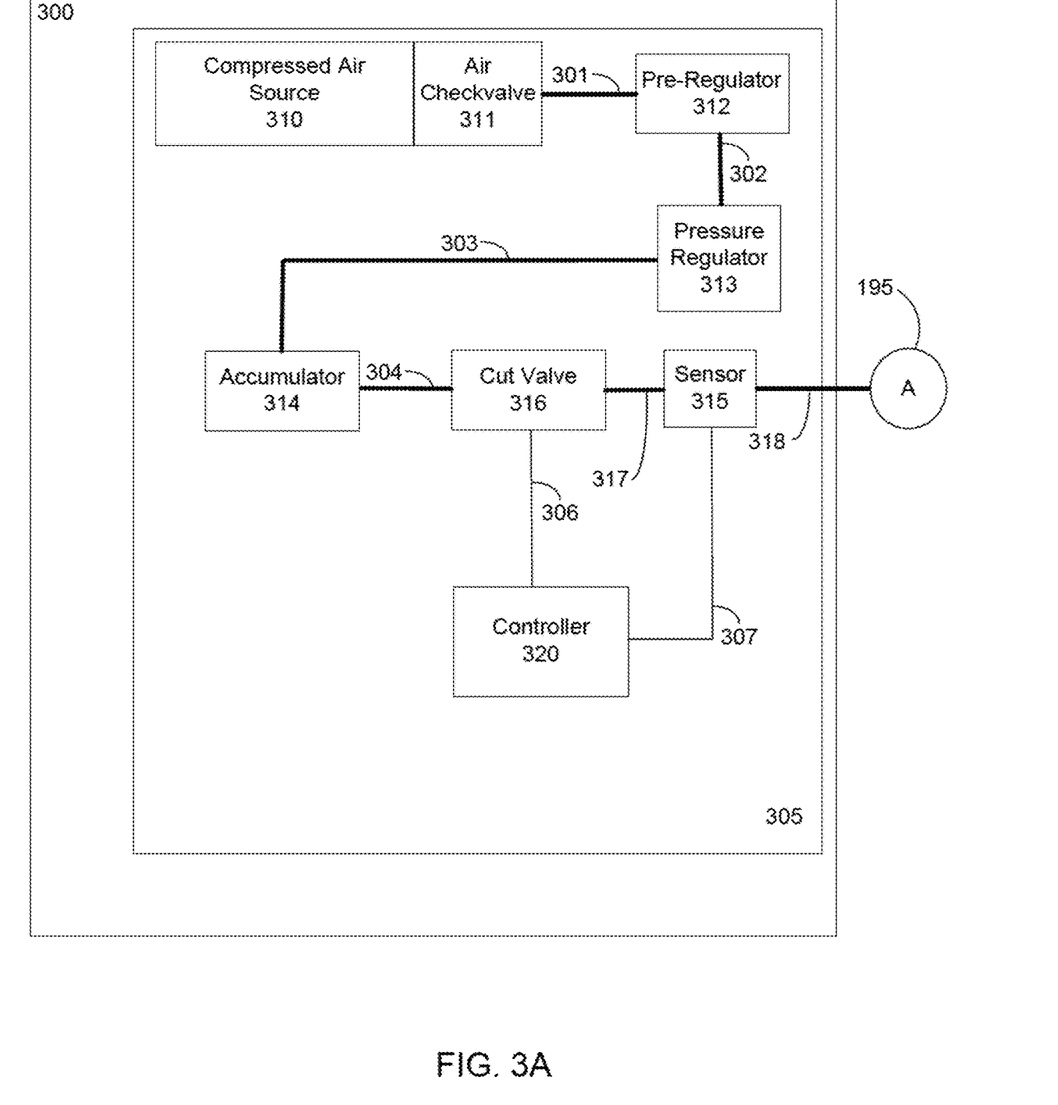
FIG. 3A is a block diagram illustrating components and devices for a pneumatic vitreous cutting module integrated within a phacoemulsification machine in accordance with the present design.

FIG. 3A is a block diagram illustrating components and devices for a Pneumatic Vitreous Cutting Module 305 integrated within a Phacoemulsification Machine 300 in accordance with the present design. Although depicted as an integral unit, module 305 functionality may be realized by using multiple devices to perform the functionality disclosed. From FIG. 3A, a Compressed Air Source 310 and associated Air Check valve 311 may supply air pressure for Pneumatic Vitreous Cutting Module 305. The Compressed Air Source 310 typically comprises a pump (not shown) configured to both provide a pneumatic, typically a gas such as air, supply pressure to the cut valve and a vent mechanism to relieve pressure to atmospheric conditions. Compressed Air Source 310 thus provides a source of vacuum or pressure. Compressed air is provided by the pump via Delivery Line 301 illustrated between Air Check valve 311 and Pre-Regulator 312. Check valve 311 is typically arranged with two ports and may allow air pressure to flow through in one direction, from Compressed Air Source 310 to Pre-Regulator 312. The pump may pump pressurized air into a high pressure chamber, not shown, which in turn provides high pressure air to Pre-Regulator 312 via Delivery Line 301. The high-pressure chamber or Compressed Air Source 310 may provide a stable source of air at a higher pressure than the working pressure of the cutter.

As used herein, the term "pressure source" or the "Compressed Air Source" means any device or arrangement that is configured to provide a source of pressure or vacuum, including but not limited to a pump or venturi device, compressed air supply, compressed air inlet supply, or any device provided within a vitrectomy machine or originating from an external source that provides pressure or vacuum, such as a pressure source provided through a wall of a building, e.g. via a wall mounted nozzle or device, an external pressure source such as an external pump, or otherwise. The terms are therefore intended to be interpreted broadly.

Pre-Regulator 312 may provide a workable steady air pressure stream from which Compressed Air Source 310 may supply air pressure for Pressure Regulator 313 via Delivery Line 302. Pressure Regulator 313 may be preset to a desired pressure and may be configured to provide air to Accumulator 314 at a low, -steady, and safe operating pressure. Pressure Regulator 313 may connect directly to Compressed Air Source 310, typically a pump but alternately a high pressure chamber, by a delivery line and take input high pressure and regulate the air pressure to a lower value consistent with the operating pressure of the cutter handpiece.

Accumulator 314 may operate as a working pressure chamber, and may receive pressurized air at specific pressure and volume from Pressure Regulator 313 via Delivery Line 303. Accumulator 314 may provide a specific amount of air pressure at a predetermined volume to Cut Valve 316 via Delivery Line 304 such that no excess pressure is forced into the Delivery Line 317.

Controller 320, which may provide a graphical user interface, computes a cut rate based on physician input and electronically provides a desired or computed cut rate to Cut Valve 316 via communications Control Line 306. The Controller 320 may take different forms, including comprising a PCBA (printed circuit board assembly), or may be part of a PCBA, ASIC, or other hardware design. A storage unit (not shown) may be provided to store certain values used by the Controller 320 during the vitrectomy procedure, including settings desired by the surgeon and other relevant data. Cut Valve 316 may open and close in response to the control signal provided from Controller 320. Controller 320 electronically controls the valves operating the regulated pressure and/or vacuum air sent to the cutter. The handpiece blade motion may move in a forward and backward reciprocating motion in response to the pressure waveform provided via Cutter Tubing 317.

Sensor 315 may monitor the pressure coming from Cut Valve 316 via Delivery Line 317. Sensor 315 may operate to determine the pressure in Delivery Line 317, and as shown is located between Cut Valve 316 and the cutter (not shown).

During operation, Controller 320 may operate Cut Valve 316 to deliver a pulse of regulated air pressure to Delivery Line 317, sensor 315, Cutter Tubing 318, and cutter (not shown). While the surgeon or practitioner may select variations in the pulse repetition frequency, once the selection is made, the system seeks to attain the desired cutting rate, subject to the discussions herein relating to optimizing cutting operation.

Cut Valve 316 is electronically controlled by Controller 320 to transmit pressure, and Cut Valve 316 opens and closes at a precise time to allow air at a specific pressure and volume to fill the Cutter Tubing 317 and operate the cutter. Cut Valve 316 may connect to atmospheric pressure for purposes of venting air received from Cutter Tubing 317. Controller 320 may provide an electronic indication to Cut Valve 316 that originates with a user selected switch, such as a switch on the handpiece, graphical user interface, or a foot switch.

Of particular note in the present design is the connection between Sensor 315 and Controller 320 shown as Line 307. This connection enables use of sensed pressure from Cut Valve 316 to be employed to determine precise commands transmitted to Cut Valve 316. Controller 320 may employ pressure sensed, and/or changes in pressure over periods of time, and/or pressure thresholds being exceeded to accurately control overall performance of the system.

Figure 3B:
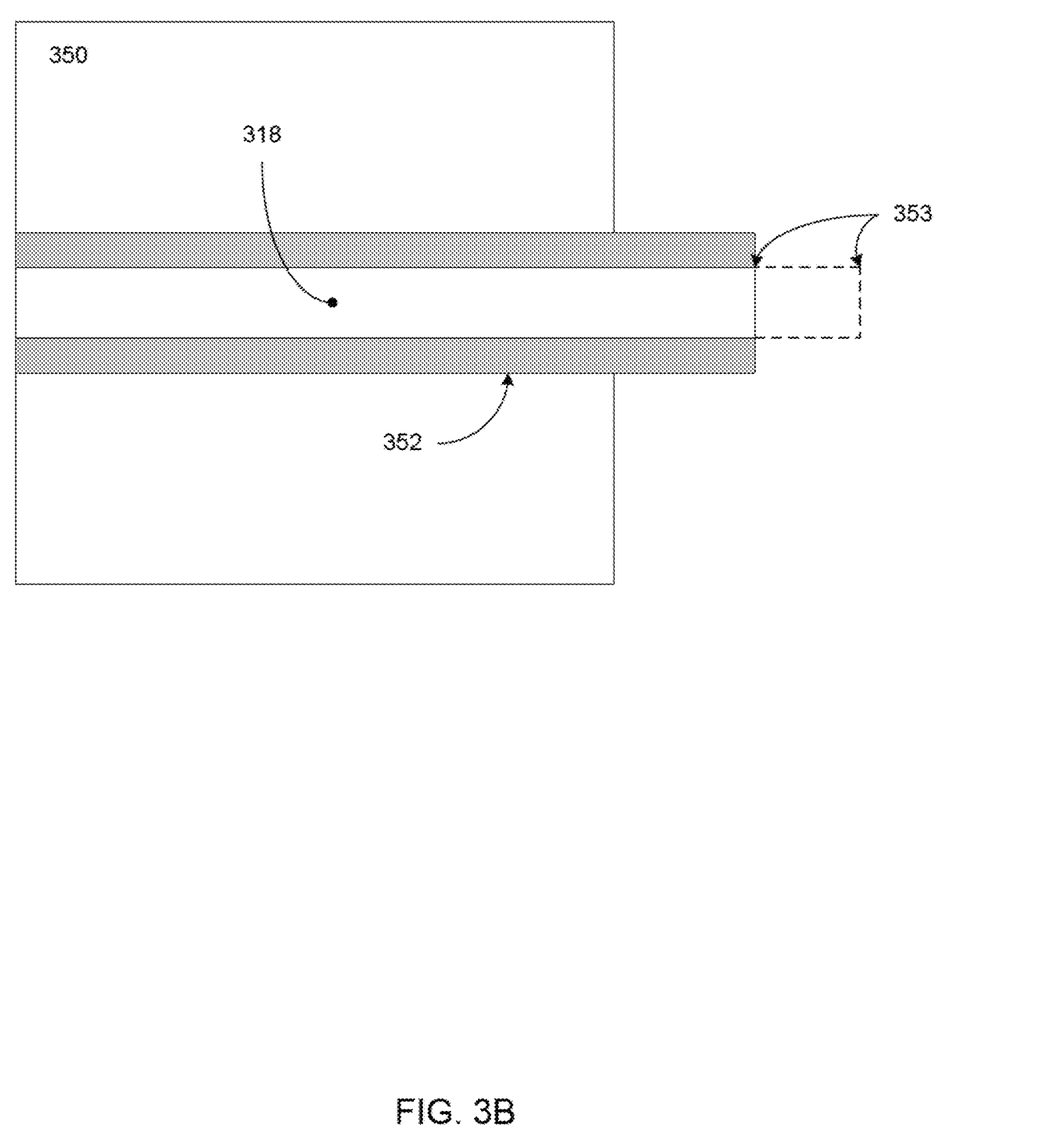
FIG. 3B illustrates a handpiece used in the vitrectomy procedure intended to be used with the variable pressure pneumatic vitrectomy control.

FIG. 3B illustrates a handpiece used in the vitrectomy procedure that may be operated with the variable pressure pneumatic vitrectomy control. From FIG. 3B, Cutter Tubing 318 is positioned within an outer passageway 352, and the handpiece 350 and pneumatics described above drive the end of cutter tubing 353 back and forth to cut vitreous material. Cutter Tubing 318 may have a uniform inner and outer diameter.

The present design employs feedback of various parameters and operation specifically tailored to operation under the specified conditions encountered based on the parameters fed back and values thereof. The present description is divided into three general sections: Regulating and optimizing vitrectomy cut pressure, monitoring amount of material cut to optimize the cutting process, and determining peak and trough pressures to accurately control vitrectomy cutting.

Determination of Cut Pressure

As noted, the vitrectomy system includes a pneumatic pressure supply, a cut valve, and a vitrectomy cutter. In operation, previous designs have provided a desired cut speed, translated into a desired on and off timing of a valve used to provide pressure and vent pressure applied to the bladder. Operation can vary due to pressure issues and mechanical issues, and to compensate for inherent mechanical issues, a certain amount of additional pressure had been applied, and/or additional time allocated to retracting the cutter. This compensation based on conjecture tended, in certain circumstances, to produce inefficient cuts.

The present design addresses the cutting inefficiencies by introducing a pressure sensing arrangement and a pressure feedback control arrangement. The present design includes a pressure sensor/transducer and a pressure controller that provide closed-loop operation and further provide an ability to sense pressure and alter performance based on desired performance criteria.

Figure 4:
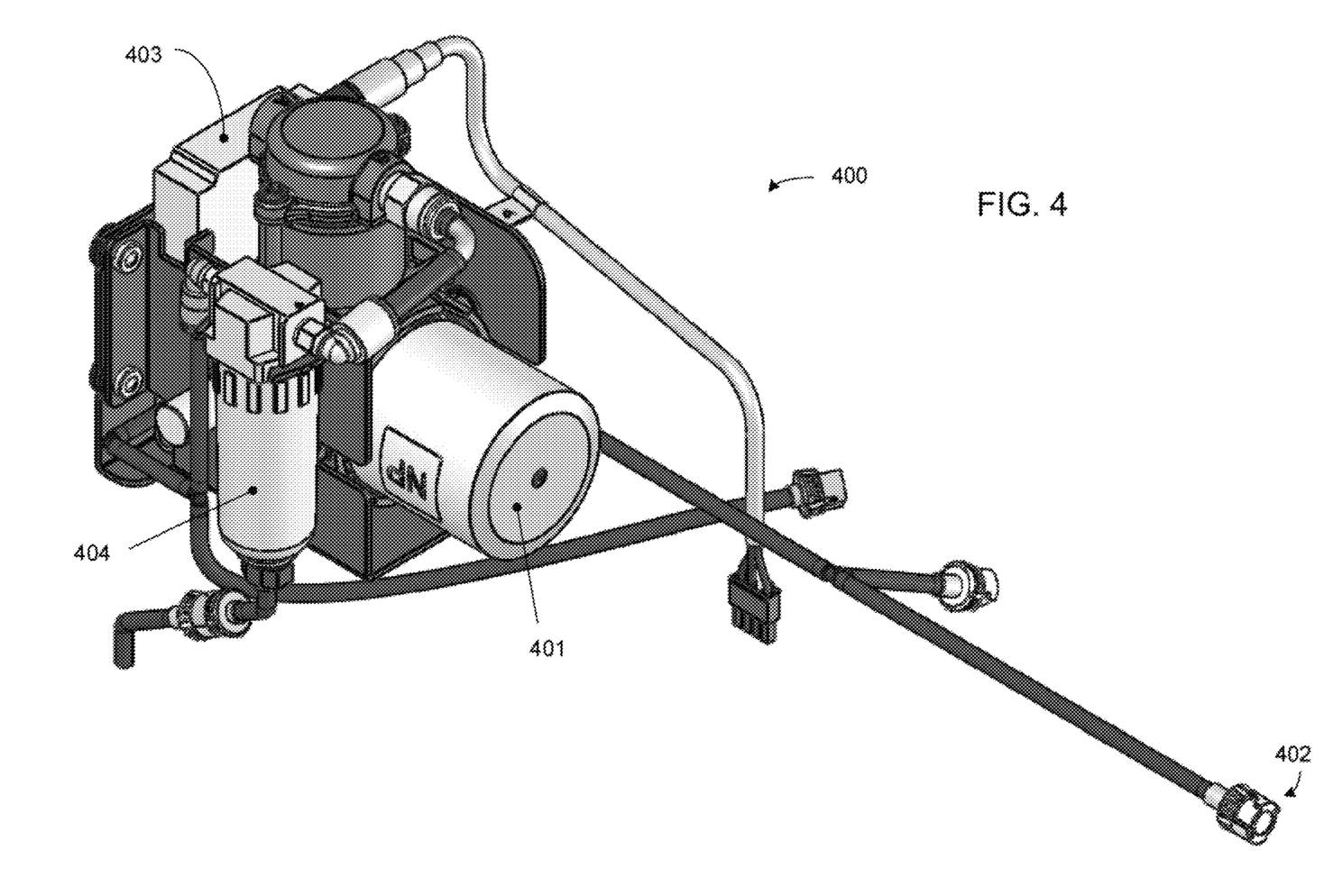
FIG. 4 is a view of a pressure source in the form of a pump employable in the present design.

FIG. 4 is a view of the various pump components, generally referred to as pump 400. Pump 400 includes pump core 401 and pump 400 provides pressure via line 401 and nozzle 402. Also shown in this view are electronic pressure regulator 403 and air filter 404. Electronic pressure regulator 403 is employed to regulate the amount of pressure supplied by the pump core 401, while air filter 404 filters the air that is provided to the pump core 401. An oxygen or air source may be provided (not shown), and this source feeds air filter 404.

Figure 5:
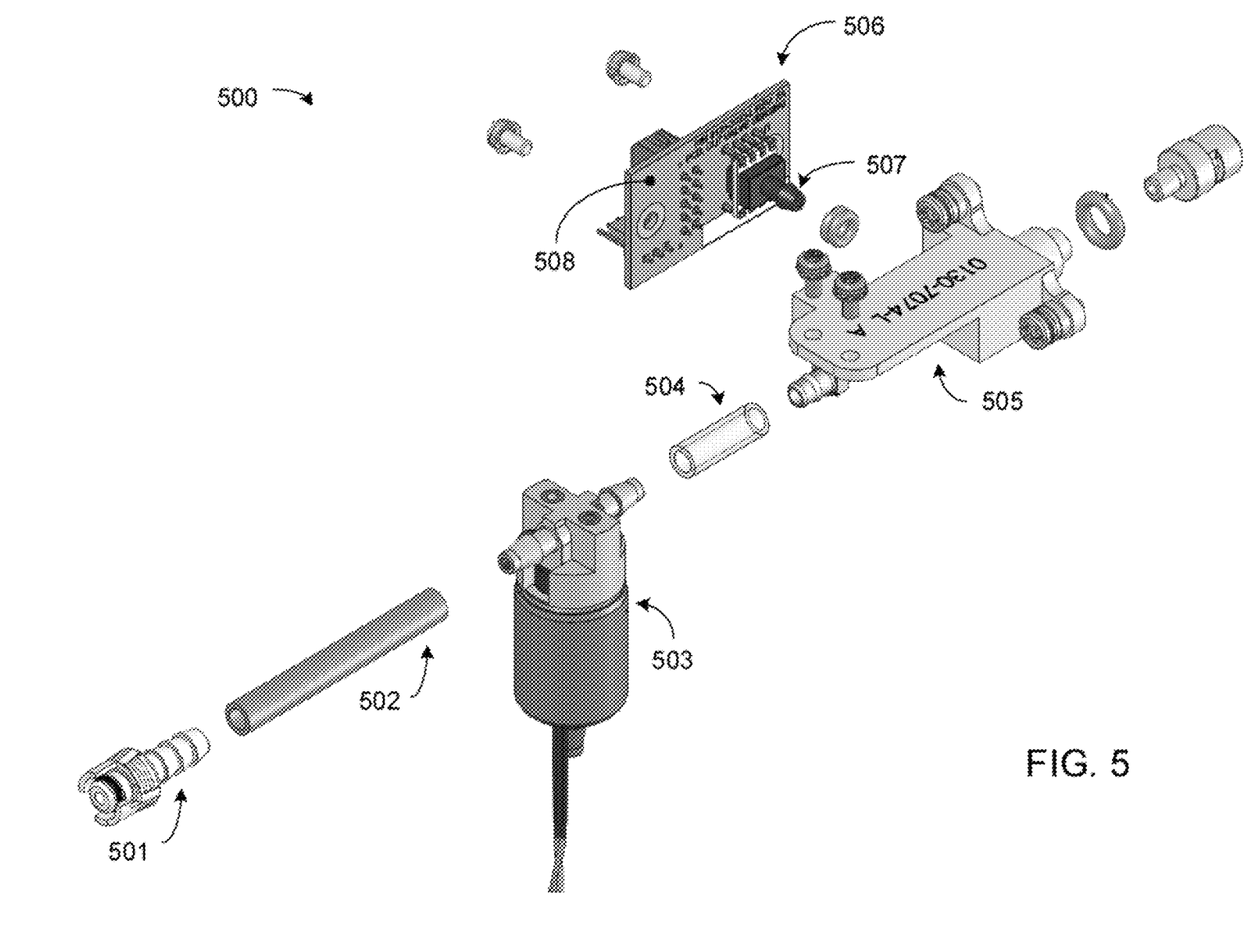
FIG. 5 shows an exploded view of a valve and sensor manifold assembly employed in the present design.

FIG. 5 illustrates the valve and sensor manifold 500. From FIG. 5, the nozzle 501 mates with nozzle 402 in FIG. 4, and line 502 connects to cut valve 503. A small section of tubing 504 is provided that connects the cut valve 503 to the pneumatic manifold 505. Pneumatic manifold 505 enables mounting of the various components illustrated to a vitrectomy device as well as passage of pumped gas. Pneumatic manifold 505 includes an opening, not shown in this view, enabling the pressure sensor/transducer 506 to be introduced. Pressure sensor/transducer 506 includes a nozzle 507 and a printed circuit board 508 that enables sensing of pressure and conversion of the sensed pressure to an electrical value. Placement of the pressure sensor/transducer 506 between the cut valve 503 and the vitrectomy handpiece (not shown) enables monitoring of the precise pressure being delivered to the cutter at all times.

Figure 6:
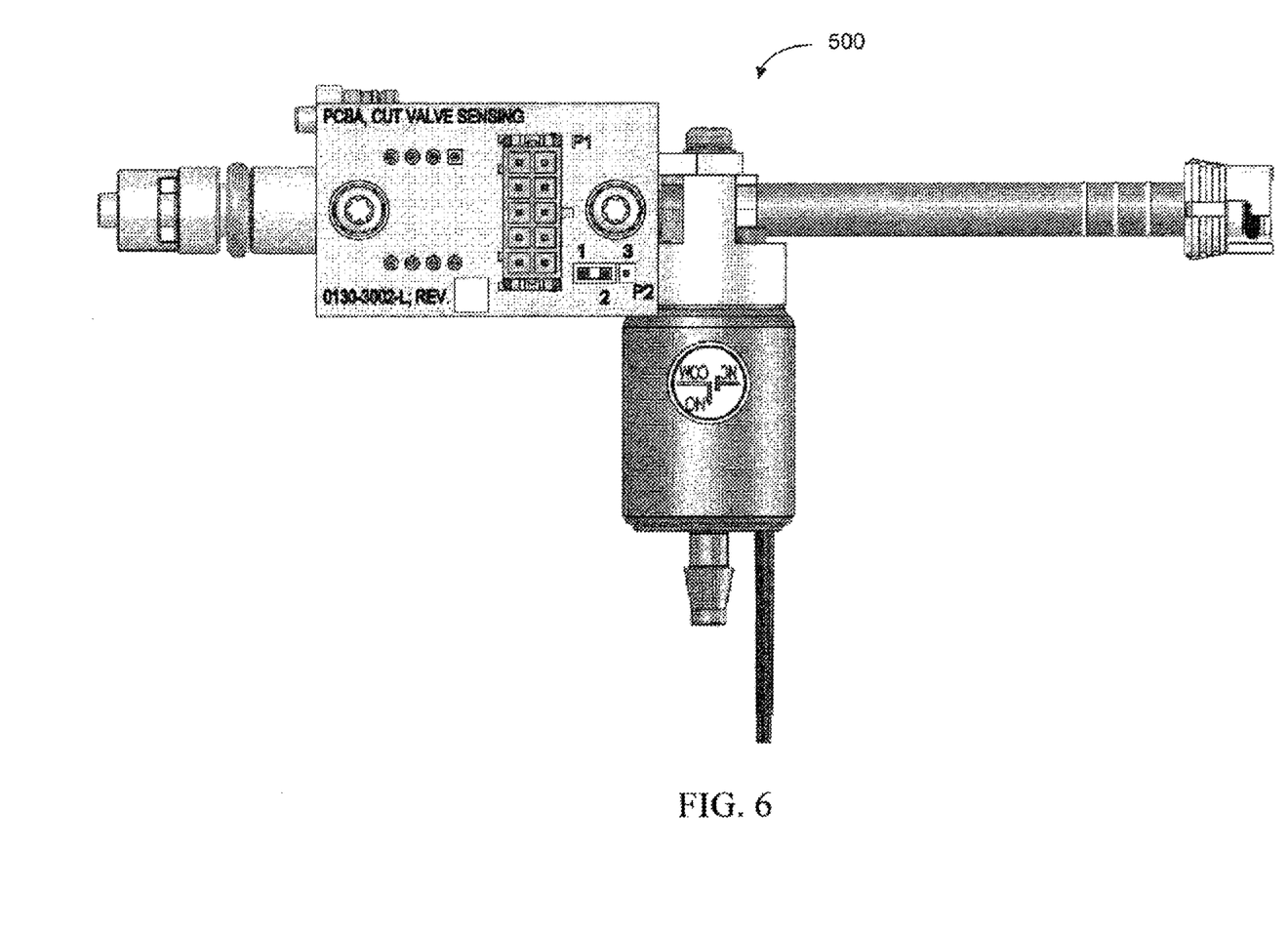
FIG. 6 illustrates the valve and sensor assembly assembled for use.
Figure 7:
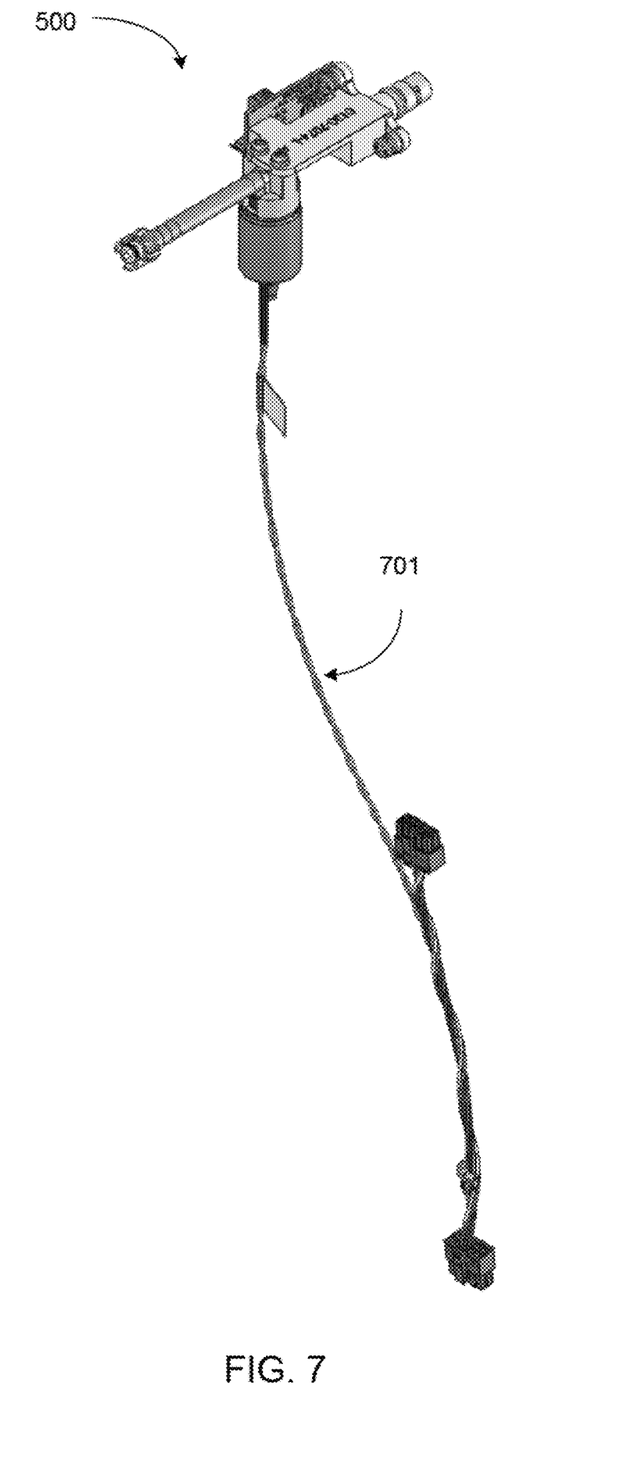
FIG. 7 is the valve and sensor assembly including associated wiring.

The combination sensor and pressure transducer in this arrangement provides closed loop monitoring of the actual delivery pressure encountered, allowing compensation for variations in cut valve performance and supply pressures. In short, the combination sensor and pressure transducer receives and determines the pressure in the line and determines when to turn the cut valve on and off. FIG. 6 shows the assembled valve and sensor manifold 500, while FIG. 7 shows the valve and sensor manifold 500 with cord 701 extending therefrom. Cord 701 provides power to the cut valve 503 as well as the combination sensor and pressure transducer 506, which includes printed circuit board 508.

With respect to the printed circuit board 508, the functionality required is fairly straightforward in that the circuitry must monitor the pressure coming though nozzle 507 and convert received pressure into an electronic signal or value, such as a number of psi (pounds per square inch) or other value. Based on the desired performance, such as the performance described below, the printed circuit board illustrated or another electronic device, such as another printed circuit board, provides signals to turn on and off cut valve 503. The inputs monitored and the logic implemented in the printed circuit board arrangement, including printed circuit board 508, is discussed below.

The arrangement of FIGS. 5-7 in addition to the pump of FIG. 4 enable detection of certain pressure values, including detecting whether pressure changes have occurred over a period of time, whether pressure has reached certain thresholds, and other pressure related parameters usable in the vitrectomy procedure. Monitoring of pressure during the cutting phase, when extending the probe, allows for an improved pressure being supplied to the cutting device, which eliminates the need to provide excess pressure or alter timing to compensate for mechanical issues. Such pressure monitoring can result in the cutter start cycle beginning sooner, allowing more material to enter the cutter for processing during a next cycle, and can provide increased benefits for cutting port opening time.

Thus the present design includes a vitrectomy apparatus having a pump, a cut valve connected to the pump, the cut valve configured to be turned on and off to provide pressure to selectively extend and retract a vitrectomy cutting device, a sensor configured to sense pressure provided from the cut valve, and a controller configured to control the cut valve based on pressure sensed by the sensor.

Monitoring of Material Processed

Using the foregoing apparatus, the surgeon or user may wish to monitor the amount of vitreous material brought into the cutter. The inability to monitor the amount of material provided to the cutter can result in more or less material cut than is desired. Failure to cut sufficient material decreases the efficiency of the vitrectomy procedure, while cutting too much material can harm the patient.

The present design also monitors two thresholds, the opening pressure threshold and the closing pressure threshold. Monitoring of opening pressure ensures that the opening pressure threshold has been achieved and the cutter is open, while monitoring of the closing pressure ensures that the closing pressure threshold has been achieved such that the vitrectomy cutter is closed. While the cutter is open, aspiration takes place and material is drawn into the central lumen of the cutter.

The present design also monitors the pressure supplied to the vitrectomy cutter to determine when the cut pressure is between the opening pressure threshold and the closing pressure threshold. Once the cut pressure goes below the opening pressure threshold, the system determines the amount of time elapsed for the cut pressure being between the opening pressure threshold and the closing pressure threshold, called the dwell time parameter. The dwell time parameter corresponds to the amount of material brought into the cutter during each cut cycle. The dwell time and aspiration rates are used to regulate the amount of material processed by the cutting device. For example, a high aspiration rate in the presence of a given dwell time indicates more material is being processed, while a low aspiration rate in the presence of the same given dwell time results in less material being processed. The design therefore takes these parameters (opening pressure threshold, closing pressure threshold, cut pressure, dwell time, and aspiration) and determines the amount of material processed based on these values. Such monitoring and information may be provided to the user or surgeon, resulting in excision of a desired amount of material processed.

Figure 8:
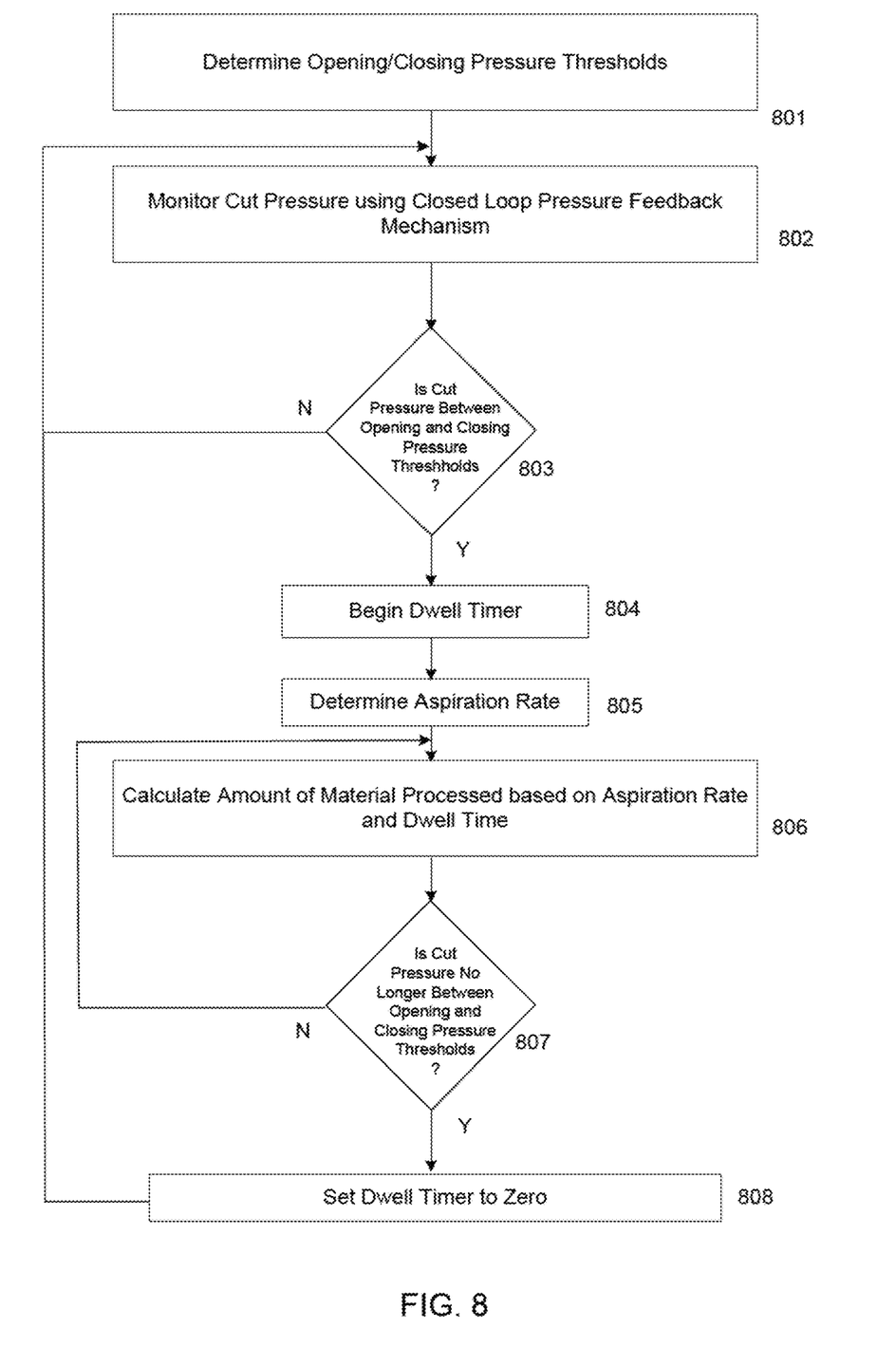
FIG. 8 is a flowchart of operation according to one embodiment of the present design.

FIG. 8 illustrates operation of the present aspect of the design. From FIG. 8, the system determines opening and closing pressure thresholds at point 801 and begins monitoring the cut pressure using the closed loop pressure feedback mechanism described above and illustrated in FIGS. 4-7 at point 802. At point 803, the system determines whether the cut pressure is between the opening and closing pressure thresholds. If not, the system continues to monitor cut pressure; if so, the system begins a dwell timer indicating the amount of time the cutter is open at point 804. At point 805, the system determines the aspiration, and at point 806, the system calculates the amount of material processed based on aspiration rate and dwell time. Point 807 assesses whether the cut pressure is no longer between the opening and closing pressure thresholds, and if so, sets the dwell timer to zero at point 808 and loops back as shown. If the cut pressure remains between the opening and closing pressure thresholds, the system loops back as shown.

The values determined may be employed to control vitrectomy cutting. For example, if more material needs to be cut where the system is operating at a given aspiration rate and a given dwell time, aspiration rate or cut rate may be increased as long as safe operation is maintained and risks of such controlled or automatic changes are acceptable.

Determination and Use of Specific Pressure Values

As noted, previous designs have operated open loop, without any type of pressure feedback. Such systems typically used control algorithms employing assumptions of errors encountered during the cutting procedure, and in certain instances provided excess pressure to extend the cutting blade and/or excess time to retract the cutting blade. Such operation represents a "best guess" as to expected cutting operation, including buffers seeking to compensate for pressure and/or timing uncertainties encountered in the cutting operation.

The present design illustrated in FIGS. 4-7 provides pressure feedback, and the design seeks to optimize cutting, namely advancing the cutting blade beginning at a point when pressure is lowest and retracting the blade at a point when pressure is the greatest. In the design of FIGS. 4-7, an electronic signal is provided to open and close the cut valve, where the signal is a pulse width modulated signal that had been generated from desired cuts per minute set by the user. The present design still obtains a desired number of cuts per minute from the user, but seeks to make the cuts in the most effective way possible.

To perform an accurate cutting, the present system maintains two pressures, namely peak pressure and trough pressure. Peak pressure is the maximum pressure attained after the command has been given to retract the blade, and represents a maximum expected pressure that will be encountered. An initial peak pressure may be provided or programmed into the vitrectomy device, or the maximum pressure may be employed when the first retraction occurs and changed as necessary at a later time. If the peak pressure measured during a given retraction of the cutting blade is greater than the peak pressure maintained by the system, the system replaces the maintained peak pressure value with the most recently encountered peak pressure value. In this manner the highest peak pressure encountered will always be maintained.

Conversely, trough pressure is the minimum pressure encountered after the command has been given to advance the blade. An initial trough pressure may be provided or the first trough pressure encountered may be stored as the baseline trough pressure. If the trough pressure measured during a given extension period is less than the trough pressure maintained by the system, the system replaces the maintained trough pressure value with the most recently encountered trough pressure value. Such operation ensures that the lowest trough pressure encountered during a procedure is employed.

The system also operates a timer such that the time between sending the command to extend or retract the cutting blade and acquisition of the peak or trough pressure can be measured. The time between a command and the system attaining either peak or trough pressure may also be maintained in the system.

With the highest encountered peak pressure and lowest encountered trough pressure, the system can act to accurately initiate cut blade extension and retraction times. As an example, assume that the peak pressure encountered during a current procedure is X psi and the time between the command and the system attaining this peak pressure is Y milliseconds. If the desired cut rate is Z cuts per second, the system anticipates that after a command to retract the blade, it will take Y milliseconds to reach a peak pressure X psi. The system thus alters the timing of the retract command such that the system will retract the blade at the time when peak pressure will occur.

Alternately, the system may monitor current pressure and may use the maintained peak pressure and trough pressure as triggers. In this embodiment, if the command has not been given by the time the peak pressure or trough pressure has been attained, the system issues the retract or extend command.

As a further option, the system may, for example, determine a maximum pressure of X psi occurs Y milliseconds after issuing a retract command. The system may monitor the pressure encountered when the command issues, which may be, for example, 0.9*X. Should the system encounter this 0.9*X pressure at a time after an extend command has been given, the system may issue the retract command, seeking to obtain the maximum maintained pressure at a desired time.

Such variations give the operator the ability to have a higher level of confidence that cuts (extensions and retractions of the blade) will occur at or near an optimal time based on the commanded cut rate. Thus the present system includes a vitrectomy apparatus having a pump, a cut valve connected to the pump, the cut valve configured to be turned on and off to provide pressure to selectively extend and retract a cutting device, a sensor configured to sense pressure provided from the cut valve, and a controller configured to control the cut valve based on pressure sensed by the sensor, wherein the controller monitors encountered pressures and alters cut valve timing based on pressure conditions previously encountered.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A vitrectomy apparatus, comprising:
a pressure source;
a cut valve connected to the pressure source, the cut valve configured to be turned on and off to provide pressure to selectively extend and retract a vitrectomy cutting device;
a sensor configured to sense pressure provided from the cut valve; and
a controller configured to control operation of the cut valve based on pressure sensed by the sensor;
wherein the cut valve is pneumatically connected to the sensor and electronically connected to the controller, wherein the controller is configured to monitor pressures encountered and alter cut valve timing based on pressure conditions previously encountered, and the controller is configured to monitor and maintain a peak pressure value and trough pressure value encountered, wherein peak pressure encountered represents a maximum pressure encountered and trough pressure comprises a minimum pressure encountered, wherein the peak pressure value is updated with a most recently encountered peak pressure value if the most recently encountered peak pressure value is greater than the peak pressure value, and the trough pressure value is updated with a most recently encountered trough pressure value if the most recently encountered trough pressure value is less than the trough pressure value.

2. The vitrectomy apparatus of claim 1, wherein the controller is further configured to alter cut valve timing based on a pressure encountered relative to the peak pressure value and the trough pressure value.

3. The vitrectomy apparatus of claim 2, wherein the controller is further configured to monitor a time following transition between issuing a command to the cut valve and one from the group consisting of the peak pressure value and the trough pressure value, and altering a future command time for a future command issued to the cut valve based on the time following transition.

4. The vitrectomy apparatus of claim 3, wherein the controller is further configured to issue the command to the cut valve when a pressure encountered reaches a threshold pressure calculated based on the time following transition and one from the group consisting of peak pressure value and the trough pressure value.

5. The vitrectomy apparatus of claim 1, wherein the controller is configured to set the peak pressure to be a presently encountered peak pressure when the presently encountered peak pressure is greater than any previously encountered peak pressure, or to set the trough pressure to be a presently encountered trough pressure when the presently encountered trough pressure is less than any previously encountered trough pressure.

6. A vitrectomy apparatus, comprising:
   a pressure source;
   a cut valve connected to the pressure source, the cut valve configured to be turned on and off to provide pressure to selectively extend and retract a vitrectomy cutting device;
   a sensor configured to sense pressure provided from the cut valve; and
   a controller configured to control operation of the cut valve based on pressure sensed by the sensor;
   wherein the cut valve is pneumatically connected to the sensor and electronically connected to the controller, wherein the controller is configured to monitor pressures encountered and alter cut valve timing based on pressure conditions previously encountered, and the controller is configured to monitor and maintain a peak pressure value and trough pressure value encountered, wherein peak pressure encountered represents a maximum pressure encountered and trough pressure comprises a minimum pressure encountered, wherein the controller is further configured to monitor and measure a time between sending a command to the cut valve and acquisition of at least one of the peak pressure value and the trough pressure value.

7. The vitrectomy apparatus of claim 6, wherein the command is at least one of to extend the vitrectomy cutting device and to retract the vitrectomy cutting device.

8. The vitrectomy apparatus of claim 6, wherein the controller is further configured to alter cut valve timing based on the time monitored between sending the command to the cut valve and acquisition of at least one of the peak pressure value and the trough pressure value.

* * * * *